United States Patent [19]

Funaki et al.

[11] 4,379,921
[45] Apr. 12, 1983

[54] PRODUCTION OF TRIAZOLYLVINYL KETONES

[75] Inventors: Yuji Funaki, Toyonaka; Shizuya Tanaka, Minoo; Noritada Matsuo, Itami, all of Japan

[73] Assignee: Sumitomo Chemical Company, Limited, Osaka, Japan

[21] Appl. No.: 292,631

[22] Filed: Aug. 13, 1981

[30] Foreign Application Priority Data

Aug. 21, 1980 [JP] Japan ................................ 55-115682
Aug. 21, 1980 [JP] Japan ................................ 55-115683
Aug. 22, 1980 [JP] Japan ................................ 55-116176
Aug. 25, 1980 [JP] Japan ................................ 55-117184
Aug. 25, 1980 [JP] Japan ................................ 55-117186

[51] Int. Cl.$^3$ .......................................... C07D 249/08
[52] U.S. Cl. .................................... 542/458; 568/325; 548/262
[58] Field of Search ........................................ 542/458

[56] References Cited

U.S. PATENT DOCUMENTS 3,972,891  8/1976  Kramer et al. .
4,182,862  1/1980  Chan ................................. 548/262
4,203,995  5/1980  Funaki et al. .

FOREIGN PATENT DOCUMENTS 2331  6/1979  European Pat. Off. ............ 548/262
2838847  3/1979  Fed. Rep. of Germany .

Primary Examiner—John M. Ford
Assistant Examiner—Bernard Dentz

Attorney, Agent, or Firm—Stevens, Davis, Miller & Mosher

[57] ABSTRACT

A process for producing a triazolylvinyl ketone compound of the formula:

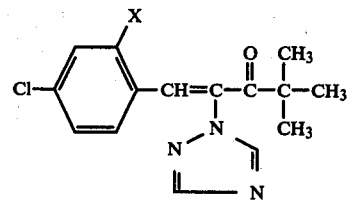

wherein X is a hydrogen or chlorine atom, comprising heating a compound of the formula:

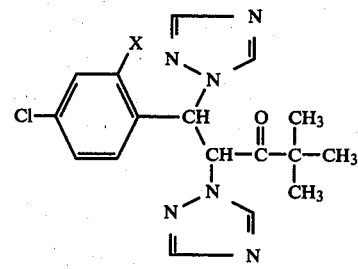

wherein X is as defined above.

The triazolylvinyl ketone compound is useful as agricultural fungicides.

21 Claims, No Drawings

PRODUCTION OF TRIAZOLYLVINYL KETONES

The present invention relates to a process for producing an antimicrobial triazolylvinyl ketone derivative.

More particularly, it pertains to an improved process for the production of a fungicidal triazolylvinyl ketone compound of the formula:

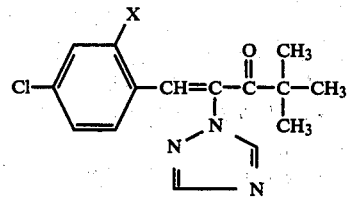

wherein X is a hydrogen or chlorine atom, and to an intermediate compound used therein.

It has been known that the said triazolylvinyl ketone compounds of the formula (I) are useful as agricultural fungicides [Japanese Patent Publication (unexamined) No. 130661/1978].

It has also been known that these compounds are useful as the intermediates for the production of fungicidal triazolylvinyl alcohol compounds of the formula:

wherein X is as defined above [U.S. Pat. No. 4,203,995; Japanese Patent Publication (unexamined) No. 41875/1979].

In view of the excellent fungicidal property of these compounds, we have intensively studied on the commercial production of these compounds, and found that the said triazolylvinyl ketone compounds can readily and advantageously be prepared in a high yield by the following method:

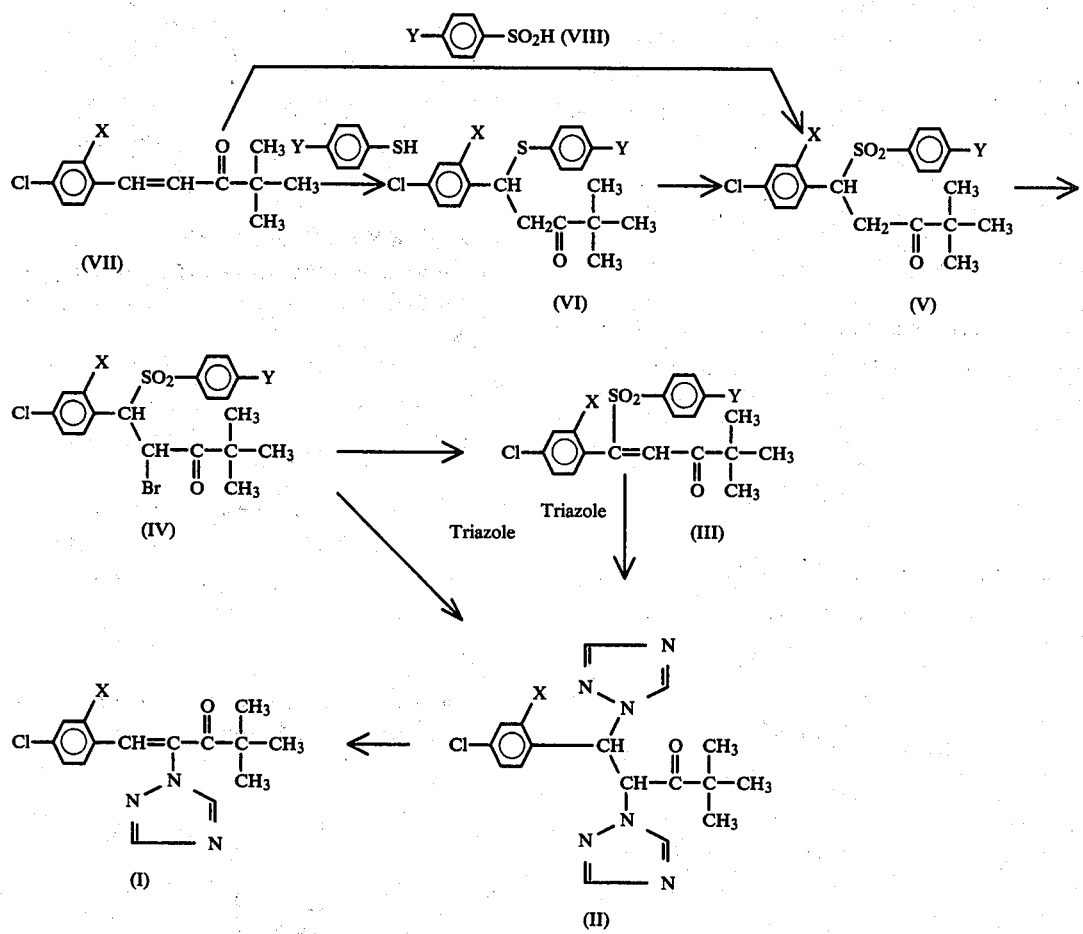

wherein X means a hydrogen or chlorine atom, and Y means a hydrogen or chlorine atom or a methyl group.

In the synthetic method of the present invention, the triazolylvinyl ketone compounds (I) can be obtained from benzalpinacolone compounds (VII) by the 4, 5 or 6 step-operation as shown in the above scheme, and each of these steps affords good yield.

The starting material, benzalpinacolones (VII) can readily be prepared by the condensation of benzaldehyde derivatives and pinacolone in an almost quantitative yield in a conventional manner. Other advantageous aspect of the process of the present invention is that phenylsulfinic acids and triazole can be recovered and recycled to minimize the consumption of these reagents in the process.

Thus, the present invention provides a process for producing a compound of the formula:

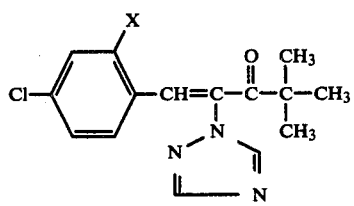
(I)

wherein X is a hydrogen or chlorine atom, which process comprises the steps of:

(a) reacting a benzalpinacolone derivative of the formula:

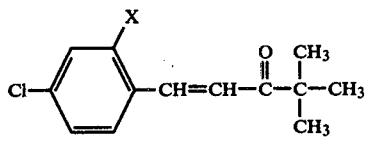
(VII)

wherein X is a hydrogen or chlorine atom, with a compound of the formula:

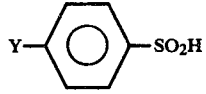
(VIII)

wherein Y is a hydrogen or chlorine atom, or a methyl group, to give a compound of the formula:

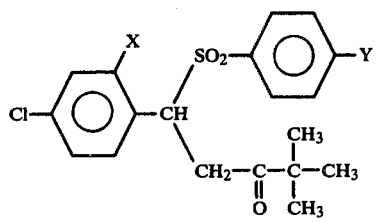
(V)

wherein X is as defined above, or with a compound of the formula:

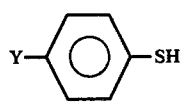
(IX)

wherein Y is as defined above, to give the compound of the formula:

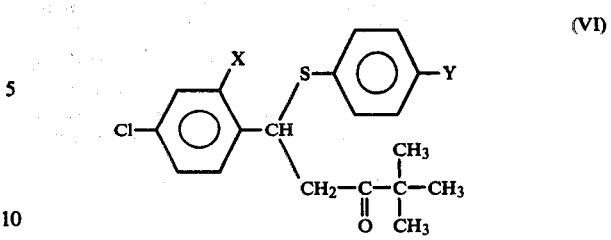
(VI)

wherein X and Y are as defined above, which is then reacted with an oxidizing agent to give the compound of the formula (V);

(b) reacting the compound of the formula (V) with a brominating agent to give a compound of the formula:

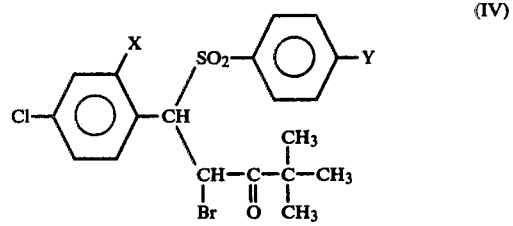
(IV)

wherein X and Y are as defined above;

(c) reacting the compound of the formula (IV) with triazole in the presence of a base to give a compound of the formula:

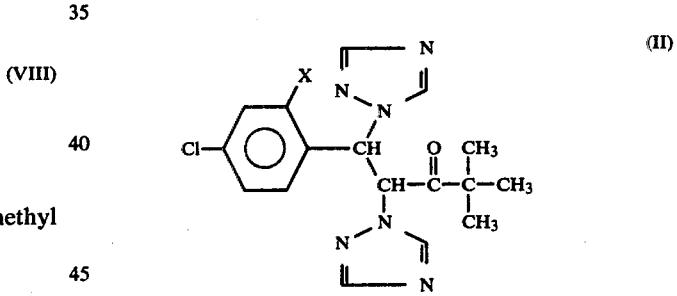
(II)

wherein X is as defined above, or with a base to give a compound of the formula:

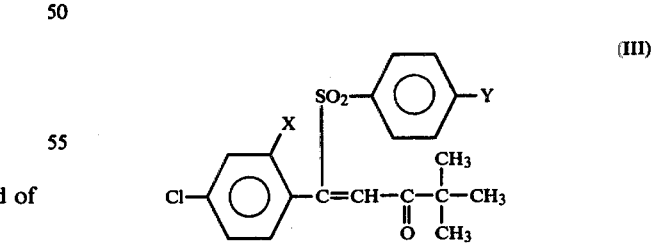
(III)

wherein X and Y are as defined above, which is then reacted with triazole to give the compound of the formula (II); and (d) heating the compound of the formula (II) to give said compounds (I).

It also provides useful intermediate compounds having the following formulae:

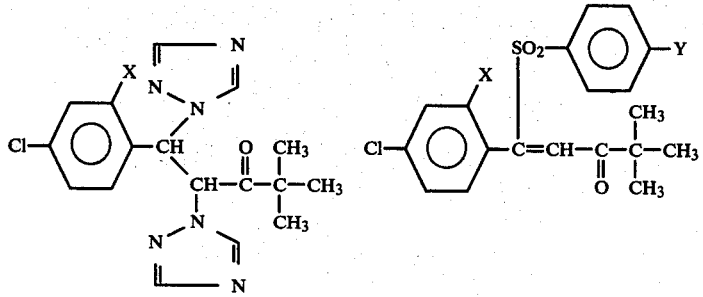

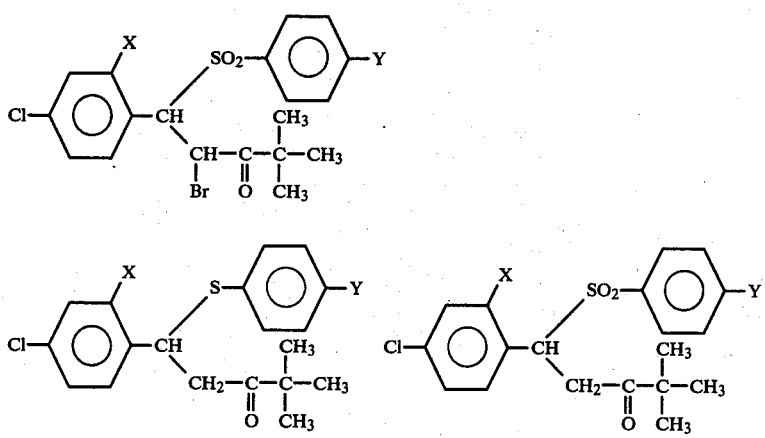

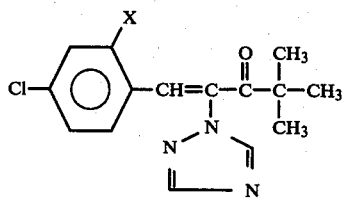

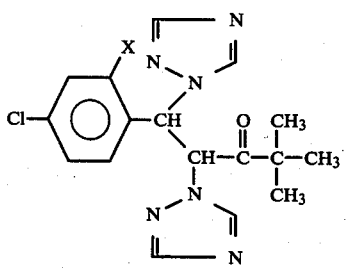

wherein X and Y are as defined above, and processes for producing the same.

The compounds of the present invention are isomeric, and it is to be understood that the present invention is contemplated to include optical and geometrical isomers thereof.

In the present invention, the compounds of the formula (I):

wherein X is as defined above, is prepared by heating the compounds of the formula (II):

wherein X is as defined above, thereby decomposing the compounds to give the desired compounds (I). This heat-decomposition process can be carried out either in a suitable solvent or without any solvent.

Examples of suitable solvents are ketone-solvents such as acetone or methyl ethyl ketone, halogenated hydrocarbons such as carbon tetrachloride, chloroform, or dichloroethane, aromatic hydrocarbons such as benzene, toluene, xylene, chlorobenzene, dichlorobenzene or trichlorobenzene, nitriles such as acetonitrile or propionitrile, ethers such as dioxane, tetrahydrofuran or diethylene glycol dimethyl ether, dimethylformamide, dimethylsulfoxide, hexamethylphosphoramide and water. The temperature at which the heating of the compound (II) is effected is in a range of from 50° C. to 200° C., preferably 80° C. to 200° C.

The products (I) may be isolated from the reaction mixture by extracting with water-immiscible solvents after diluting the reaction mixture with water. And, from the remaining aqueous layer, triazole may be recovered with high recovery rates by extracting under basic and basic conditions, respectively.

The bistriazolyl ketone compounds (II) can be prepared from the compounds of the formula (IV) by the following two methods:

The first method is the conversion of the compounds of the formula (IV) to the compounds (II) with triazole. This process is carried out by reacting the compounds (IV) with triazole in the presence of a base in a suitable solvent. Examples of the bases used in this process are carbonates such as potassium or sodium carbonates, acetates such as potassium or sodium acetates, hydroxides of metals such as potassium, sodium or calcium hydroxides, and tertiary amines such as triethyl amine or pyridine. Among these bases, carbonates are preferable.

Examples of the solvents are ketones such as acetone or methyl ethyl ketone, nitriles such as acetonitrile or propionitrile, aromatic hydrocarbons such as benzene, toluene or xylene, ethers such as tetrahydrofuran, dioxane or diethyl ether, dimethyl formamide, dimethylsulfoxide and hexamethylphosphoramide. In this process, water, alone or in combination with the said organic solvents, may also be used as a solvent. The reaction temperature may be from 0° C. to the boiling point of the used solvent, preferably from 50° C. to the boiling point of the used solvent.

Triazole is used in an amount of 2–5 moles, preferably 2–3 moles per 1 mole of the compounds (IV). The amount of the bases used in this process is 2 moles or more per 1 mole of the compounds (IV). The product is readily isolated in a conventional manner after removing the salts of the used base and hydrobromic acid and the phenylsulfinic acid compounds (VIII) by filtration or dissolving in water.

Alternatively, the compounds (II) can also be prepared by converting the compounds (IV) to the compounds (III) with a base, and then reacting the compounds (III) with triazole. More specifically, the first step can be carried out by reacting the compounds (IV) with at least equimolar amounts of a base. Examples of the bases are carbonates such as potassium or sodium carbonates, acetates such as potassium or sodium acetates, metal hydroxides such as potassium, sodium or calcium hydroxides and tertiary amines such as triethyl amine or pyridine, and carbonates and metal hydroxides are preferable. Triazole may also be used as a base in this process.

In general, it is advantageous to effect the reaction in a solvent except the case where a tertiary amine is used therein. Examples of suitable solvents are ketones such as acetones or methyl ethyl ketone, nitriles such as acetonitrile or propionitrile, aromatic hydrocarbons such as benzene, toluene or xylene, ethers such as diethyl ether, dioxane or tetrahydrofuran, dimethylformamide, dimethylsulfoxide, and hexamethylphosphoramide. The reaction may also be carried out in water, alone or in homogeneous or multiphase combination with the said solvents. The reaction temperature is usually in a range from 0° C. to the boiling point of the used solvent, but, when a strong base such as metal hydroxide is used, the reaction smoothly proceeds at such a law temperature as 0° C. or so. The amounts of the bases is usually 1 to 5 moles, preferably 1 to 3 moles per 1 mole of the compounds (IV). The isolation of the compounds (III) can readily be carried out in a conventional way, for example, by extracting with a water-insoluble solvent followed by evaporation. When the reaction is carried out in a water-soluble solvent, the reaction mixture is diluted with water, and the products are crystallized and isolated by filtration.

The second step, the conversion of thus obtained compounds (III) to the compounds (II) is accomplished by reacting the compounds (III) with triazole. This process can advantageously be effected in the presence of a base in amounts of 2 moles or more, preferably 2.05 to 5 moles per 1 mole of the compounds (III). This synthetic method can continuously be carried out without isolation of the compounds (III). Thus prepared compounds (II) can readily be isolated in a conventional manner as mentioned previously.

The compounds (IV) can be obtained by reacting the compounds (V) with a brominating agent. As a brominating agent of this reaction, bromine, N-bromosuccinimide and other brominating agents which are usually used for the bromination of ketone compounds can be used. These brominating agents are used in an amount of 1 mole or more, preferably 1 to 2 moles per 1 mole of the compounds (V). It is preferable to carry out the reaction in the presence of a solvent. Halogenated hydrocarbon such as carbon tetrachloride, chloroform or dichloroethane, halogenated aromatic hydrocarbon such as chlorobenzene or dichlorobenzene, ether such as diethyl ether, dioxane or tetrahydrofuran, water, methanol, pyridine, dimethylformamide and acetic acid can be used as a solvent. The reaction is usually carried out at a temperature of from 0° C. to the boiling point of the used solvent. The products may readily be isolated by a method conventionally used in the bromination process. For example, the reaction mixture is diluted with water, and extracted with a solvent insoluble in water or filtrating the precipitated products.

The compounds (V) may be prepared by reacting the compounds (VII) with one to 3 equimolar amounts of the compounds (VIII) in a suitable solvent at a temperature of from 0° C. to the boiling point of the used solvent. Generally speaking, the compounds (V) is prepared in a quantitative yield by this reaction. Examples of solvents suitable to this process are alcohols such as methanol, ethanol or propanol, hydrocarbons such as benzene, toluene or xylene, ketones such as acetone or methyl ethyl ketone, nitriles such as acetonitrile or propionitrile, ethers such as diethyl ether, tetrahydrofuran or dioxane, dimethylformamide, dimethylsulfoxide and the like. Mixed solvents of these organic solvents and water may also be used. When the reaction is conducted in the presence of a base such as pyridine or Triton B or sodium phosphite in amounts of 0.01 to 2.0 moles per 1 mole of the compounds (VII) a good result is obtained.

The compounds (V) may also be prepared by the oxidation of the (VI) with a suitable oxidizing agent. Examples of the oxidizing agents are hydrogen peroxide, organic acid peroxides, potassium permanganate, sodium metaperiodate, nitric acid, sodium hypochlorite, ozone, chromic acid and the like, and preferred are hydrogen peroxide, organic acid peroxides and ozone. In general, it is preferable to carry out the reaction in the presence of a solvent. Organic solvents which are inert to the used oxidizing agent, whether alone or in combination with the other inert solvents, can be used, and particularly preferred are halogenated hydrocarbons such as carbon tetrachloride, dichloro methane or chloroform, ketones such as acetone or methyl ethyl ketone, acetic acid and water. The reaction is usually carried out at a temperature of from −50° C. to 100° C., preferably −10° C. to 80° C. With respect to the amounts of the oxidizing agents, the oxidation of 1 mole of the compounds (VI) requires 2 moles of active oxygen. For example, in case of hydrogen peroxide, 2 moles is required for the oxidation of 1 mole of the compounds (VI). It is, however, desirable to use the oxidizing agent in small excess to eliminate bad odor caused by the thiophenol derivatives remaining in the compounds (VI). The isolation of the products can readily be carried out by diluting the reaction mixture with water, and extracting with a water-immiscible solvent, or crystallizing the products and collecting them by filtration.

The compounds (VI) can be prepared in a good yield by the reaction of the compounds (VII) with the compounds (IX). The reaction can be carried out in an organic solvent such as alcohols (e.g., methanol, ethanol, propanol, etc.), aromatic hydrocarbon (e.g., benzene, toluene, xylene, etc.), ketones (acetone, methyl ethyl ketone, etc.), nitriles (e.g., acetonitrile, propionitrile, etc.), ethers (e.g., diethyl ether, tetrahydrofuran, dioxane, etc.), dimethylformamide, or dimethylsulfoxide. As a solvent, aqueous mixture of these solvents may also be used. The reaction can be carried out at a temperature of from 0° C. to the boiling point of the used solvent. Generally, 1 mole of the compounds (VII) is reacted with 1 to 3 moles of the compounds (IX), preferably in the presence of a basic catalyst in amounts of 0.001 to 1 mole per 1 mole of the compounds (VII). Examples of the basic catalysts are sodium hydroxide, potassium hydroxide, sodium carbonate, potassium carbonate, sodium bicarbonate, triethylamine, dimethylaniline, pyridine, and Triton-B. The compounds (IX) may be used in the form of potassium or sodium salts for this process.

The compounds (VII) can readily be prepared by a conventional method as previously mentioned (Organic Synthesis, Col. Vol. I, p. 81, and C.A., 84: p 73606u; 63: 1726f).

The following examples are given to illustrate the present invention more precisely, but it is not intended to limit the present invention thereto.

EXAMPLE 1

Synthesis of 1-(4-chlorophenyl)-4,4-dimethyl-1-phenylthiopentan-3-one

To a mixture of 4-chlorobenzalpinacolone (22.3 g), triethylamine (5 drops) and ethanol (250 ml) was added thiophenol (12 g) and the mixture was kept to 70° C. for 4 hours. After ice-cooling, the resulted precipitates were collected by filtration, washed with cold ethanol and dried to give white crystals of the captioned compound (29 g; 84%). m.p. 127°–128° C.

| Elementary analysis | C (%) | H (%) | S (%) | Cl (%) |
|---|---|---|---|---|
| Found | 68.55 | 6.33 | 9.72 | 10.45 |
| Calculated (as $C_{19}H_{21}OSCl$) | 68.54 | 6.37 | 9.63 | 10.65 |

EXAMPLE 2

Synthesis of 1-(4-chlorophenyl)-4,4-dimethyl-1-phenylsulfonylpentan-3-one 1-(4-Chlorophenyl)-4,4-dimethyl-1-phenylthiopentan-3-one (18 g) was dissolved in chloroform (500 ml). m-Chloroperoxybenzoic acid (24 g) was gradually added to the mixture in 1 hour. The mixture was then stirred at 20° C. for 3 hours. The mixture was washed with 5% sodium hydrogen sulfite aqueous solution and sodium bicarbonate aqueous solution, and concentrated. The solid residue was then treated with ethanol to give crystals, which were collected by filtration and dried to give 18.8 g of the captioned compound. m.p. 145°–146° C.

| Elementary analysis | C (%) | H (%) | S (%) | Cl (%) |
|---|---|---|---|---|
| Found | 62.71 | 5.73 | 8.86 | 9.64 |
| Calculated (as $C_{19}H_{21}O_3SCl$) | 62.53 | 5.81 | 8.79 | 9.71 |

EXAMPLE 3

Synthesis of 2-bromo-1-(4-chlorophenyl)-4,4-dimethyl-1-phenylsulfonylpentan-3-one 1-(4-Chlorophenyl)-4,4-dimethyl-1-phenylsulfonylpentan-3-one (5.0 g) was dissolved in a mixture of 100 ml of chloroform and 100 ml of acetic acid. To this solution, 2.2 g of bromine was added dropwise at 50° C. The mixture was kept at 50° C. for 3 hours and then washed with ice-water and an aqueous solution of sodium bicarbonate. The chloroform layer was evaporated and the solid residue was crystallized in a mixture of carbon tetrachloride and n-hexane. The crystals were collected by filtration and dried to give 5.8 g of the captioned compound. m.p. 167°–168° C.

| Elementary analysis | C (%) | H (%) | S (%) | Cl (%) | Br (%) |
|---|---|---|---|---|---|
| Found | 51.55 | 4.48 | 7.20 | 8.05 | 17.90 |
| Calculated (as $C_{19}H_{20}O_3SClBr$) | 51.42 | 4.55 | 7.22 | 7.99 | 18.00 |

EXAMPLE 4

Synthesis of 1-(4-chlorophenyl)-4,4-dimethyl-1,2-bis(1,2,4-triazol-1-yl)pentan-3-one A mixture of 1.1 g of potassium carbonate, 0.56 g of triazole and 30 ml of acetonitrile was refluxed for 1 hour, and a solution of 1.8 g of 2-bromo-1-(4-chlorophenyl)-4,4-dimethyl-1-phenylsulfonylpentan-3-one in 30 ml of acetonitrile was added thereto. The mixture was refluxed for 2 hours. After the removal of the undissolved by filtration, the mixture was concentrated. Ice water was added to the residue and extracted with chloroform. The chloroform layer was evaporated to give 1.5 g of oily substance, which was then dissolved in chloroform and crystallized by adding n-hexane. The crystals were collected by filtration and dried to give 1.38 g of the captioned compound (96%). m.p. 157°–161° C.

| Elementary analysis | C (%) | H (%) | N (%) | Cl (%) |
|---|---|---|---|---|
| Found | 57.02 | 5.38 | 23.35 | 9.73 |
| Calculated (as $C_{17}H_{19}N_6OCl$) | 56.89 | 5.35 | 23.42 | 9.88 |

EXAMPLE 5

Synthesis of 1-(4-chlorophenyl)-4,4-dimethyl-1-phenylsulfonyl-1-penten-3-one

2-Bromo-1-(4-chlorophenyl)-4,4-dimethyl-1-phenylsulfonylpentan-3-one (4.44 g) and triazole (2.76 g) were dissolved in dimethylformamide (30 ml), and the solution was refluxed for 2 hours. After cooling, it was poured into 100 ml of water and extracted with 100 ml of chloroform. The chloroform layer was washed for three times with water, dried over anhydrous sodium sulfate, and concentrated under reduced pressure. The residue was crystallized in n-hexane, and the crystals were collected by filtration and dried to give 2.65 g of 1-(4-chlorophenyl)-4,4-dimethyl-1-phenylsulfonyl-1-penten-3-one. m.p. 135°–136° C.

| Elementary analysis | C (%) | H (%) | S (%) | Cl (%) |
|---|---|---|---|---|
| Found | 62.91 | 5.35 | 8.71 | 9.65 |
| Calculated (as $C_{19}H_{19}O_3SCl$) | 62.88 | 5.29 | 8.83 | 9.77 |

It seems that triazole acts as a hydrobromic acid—capture in this reaction. On the TLC of the mother liquid of the crystallization of the product, a slight spot with the Rf value corresponding to that of the triazole-substituted compound was observed, but the compound could not be isolated. It is considered that in the absence of a base the addition of triazole to the sulfonylvinyl ketone compounds proceeds only in a very low yield even when it is conducted in excessive amounts of triazole.

EXAMPLE 6

Synthesis of 1-(4-chlorophenyl)-4,4-dimethyl-1,2-bis(1,2,4-triazol-1-yl)pentan-3-one A mixture of 1.04 g of triazole, 2.07 g of anhydrous potassium carbonate and 30 ml of acetonitrile was refluxed for 1 hour with stirring. After cooling, 4.44 g of 1-(4-chlorophenyl)-4,4-dimethyl-1-phenylsulfonyl-1-penten-3-one was added to the mixture and reacted at 25° C. for 1 hour and for 5 hours under reflux. After the removal of the undissolved by filtration, the mixture was treated in the same way as that of Example 4, and 2.52 g of the crude product was obtained. The crude product was purified by a column chromatography on silica gel to give 2.12 g of the captioned compound. m.p. 157°–161° C.

| Elementary analysis | C (%) | H (%) | N (%) | Cl (%) |
|---|---|---|---|---|
| Found | 56.70 | 5.33 | 23.50 | 9.92 |
| Calculated (as $C_{17}H_{19}N_6OCl$) | 56.89 | 5.35 | 23.42 | 9.88 |

EXAMPLE 7

Synthesis of 1-(4-chlorophenyl)-4,4-dimethyl-2-(1,2,4-triazol-1-yl)-1-penten-3-one 1-(4-Chlorophenyl)-4,4-dimethyl-1,2-bis(1,2,4-triazol-1-yl)-pentan-3-one (0.5 g) was heated at 180° C. for 1 hour and at 200° C. for 3 hours on an oil bath. After cooling, the mixture was dissolved in chloroform (50 ml), washed with water (50 ml) and concentrated to give yellow oily substance (0.37 g). Triazole (0.095 g; 99%) was recovered from the aqueous layer by concentration. The oily substance was analyzed by the gas-chromatography under the following conditions:

Apparatus: Nihon Denki 20K type FID detector
Column: 5% XE-60 Chromosorb W carrier, 1 m glass column
Column Temperature: 200° C.
Vaporizing Room temperature: 240° C.
Carrier gas pressure: 1.0 Kg/cm²

Two peaks were observed at retention times 300 sec., and 360 sec. (peak area ratio: 36/64).

| Elementary analysis of the oily substance | C (%) | H (%) | N (%) | Cl (%) |
|---|---|---|---|---|
| Found | 62.20 | 5.45 | 14.38 | 12.42 |
| Calculated (as $C_{15}H_{16}N_3OCl$) | 62.17 | 5.58 | 14.50 | 12.23 |

This elementary analysis data agrees with that of 1-(4-chlorophenyl)-4,4-dimethyl-2-(1,2,4-triazol-1-yl)-1-penten-3-one. The captioned compound has a double bond and hence is geometrically isomeric. Namely, it contains the Z-isomer, wherein the 4-chlorophenyl and triazole are in cis-position, and the E-isomer, wherein the said groups are in trans-position.

The said peaks of the gas-chromatography correspond to those of the E-isomer and Z-isomer, and the NMR-spectrum of the substance is the combination of the signals of the both isomers.

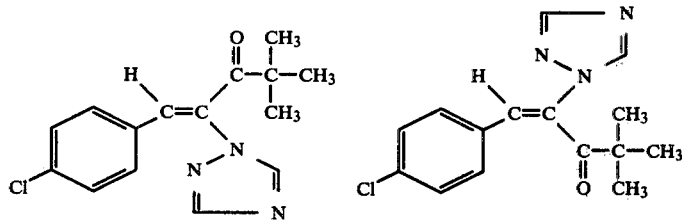

Z-Isomer
m.p. 78–79° C.

E-Isomer
m.p. 108–109° C.

The elementary analysis and NMR spectrum of each isomer are shown below. The NMR spectrum was measured with deutero chloroform as solvent, and the chemical shift was expressed by δ values with tetramethylsilane as internal standard.

E isomer of 1-(4-chlorophenyl)-4,4-dimethyl-2-(1,2,4-triazol-1-yl)-1-penten-3-one:

| Elementary analysis | C (%) | H (%) | N (%) | Cl (%) |
|---|---|---|---|---|
| Calculated (as $C_{15}H_{16}N_3OCl$) | 62.17 | 5.58 | 14.50 | 12.23 |
| Found | 62.32 | 5.60 | 14.41 | 12.20 |

NMR spectrum:
8.11 (1H, s, triazole proton)
7.90 (1H, s, triazole proton)
7.15 (4H, s, phenyl proton)
6.99 (1H, s, olefin proton)
0.99 (9H, s, butyl proton)

Z isomer of 1-(4-chlorophenyl)-4,4-dimethyl-2-(1,2,4-triazol-1-yl)-1-penten-3-one (Compound No. 1′):

| Elementary analysis | C (%) | H (%) | N (%) | Cl (%) |
|---|---|---|---|---|
| Found | 62.35 | 5.59 | 14.38 | 12.18 |

NMR spectrum:
8.14 (1H, s, triazole proton)
7.98 (1H, s, triazole proton)
7.22 (2H, d, phenyl proton, J=8 Hz)
6.73 (2H, d, phenyl proton, J=8 Hz)
7.49 (1H, s, olefin proton)
1.22 (9H, s, butyl proton)

EXAMPLE 8

Synthesis of 1-(4-chlorophenyl)-4,4-dimethyl-2-(1,2,4-triazol-1-yl)-1-penten-3-one A mixture of 0.6 g of 1-(4-chlorophenyl)-4,4-dimethyl-1,2-bis(1,2,4-triazol-1-yl)-pentan-3-one and 4 ml of 1,2,4-trichlorobenzene was reacted at 180°–190° C. for 4 hours. The reaction mixture was diluted with 50 ml of toluene and extracted with 50 ml of 1 N hydrochloric acid aqueous solution, whereby 1,2,4-triazole was recovered in the aqueous layer. The organic solvent layer was washed with 50 ml of 5% NaHCO$_3$ aqueous solution, and evaporated under reduced pressure to give 0.48 g of the captioned compound. The product was found to be a mixture of 35 parts of the E-isomer and 65 parts of the Z-isomer upon the gas-chromatographic analysis. The product was subjected to the column chromatography on silica gel (50 g) with, as an eluent, a mixture of 1 part of acetone and 20 parts of n-hexane, thereby 0.15 g of the E-isomer and 0.26 g of the Z-isomer were obtained.

EXAMPLE 9

Synthesis of 1-(2,4-dichlorophenyl)-4,4-dimethyl-1-phenylthiopentan-3-one

A mixture of 25.7 g of 2,4-dichlorobenzalpinacolone, Triton-B (4 drops) and 300 ml of ethanol was heated to 50°–60° C. Thiophenol (12.1 g) was added dropwise to the mixture and refluxed for 6 hours. The reaction mixture was concentrated, ice water was added thereto, and extracted with ether. After the removal of the ether by distillation, the oil residue was treated with n-hexane, and the resulted crystals were dried to give 30 g of the captioned compound. m.p. 79°–80° C.

| Elementary analysis | C (%) | H (%) | S (%) | Cl (%) |
|---|---|---|---|---|
| Found | 62.02 | 5.43 | 8.83 | 19.41 |
| Calculated (as C$_{19}$H$_{20}$OSCl$_2$) | 62.12 | 5.50 | 8.73 | 19.30 |

EXAMPLE 10

Synthesis of 1-(2,4-dichlorophenyl)-4,4-dimethyl-1-phenylsulfonylpentan-3-one

Method A: 1-(2,4-Dichlorophenyl)-4,4-dimethyl-1-phenylthiopentan-3-one (18.3 g) was dissolved in dichloromethane (500 ml), and m-chloroperoxybenzoic acid (19.8 g) was added to the mixture at a temperature of −5° C. The mixture was then treated with the same procedure as that of Example 2 to give 18.3 g of the captioned compound. m.p. 112°–113° C.

| Elementary analysis | C (%) | H (%) | S (%) | Cl (%) |
|---|---|---|---|---|
| Found | 57.25 | 4.96 | 8.01 | 17.67 |
| Calculated (as C$_{19}$H$_{19}$O$_3$SCl$_2$) | 57.29 | 4.82 | 8.05 | 17.80 |

Method B: 1-(2,4-Dichlorophenyl)-4,4-dimethyl-1-phenylthiopentan-3-one (9.16 g) was dissolved in acetone (200 ml), and 37% hydrogen peroxide (6.9 g) was added dropwise thereto at 20° C. The mixture was kept at 20° C. for 12 hours, at 40° C. for 1 hour and 60° C. for 1 hour. After cooling the mixture to 15° C., water (100 ml) was gradually added dropwise to it. The resulted precipitates were collected by filtration and dried to give 9.0 g of the captioned compound.

EXAMPLE 11

Synthesis of 2-bromo-1-(2,4-dichlorophenyl)-4,4-dimethyl-1-phenylsulfonylpentan-3-one To a solution of 39.9 g of 1-(2,4-dichlorophenyl)-4,4-dimethyl-1-phenylsulfonylpentan-3-one in 500 ml of chloroform, 16.8 g of bromine was added dropwise at 60° C. and the mixture was then kept at 60° C. for 4 hours. The reaction mixture was treated in the same way as that of Example 3 to give 44.5 g of crystals of the captioned compound. m.p. 135°–136° C.

| Elementary analysis | C (%) | H (%) | S (%) | Cl (%) | Br (%) |
|---|---|---|---|---|---|
| Found | 47.82 | 4.22 | 6.65 | 14.71 | 16.72 |
| Calculated (as C$_{19}$H$_{19}$O$_3$SCl$_2$Br) | 47.71 | 4.01 | 6.70 | 14.83 | 16.71 |

EXAMPLE 12

Synthesis of 1-(2,4-dichlorophenyl)-4,4-dimethyl-1-phenylsulfonyl-1-penten-3-one Method A: A solution of 9.6 g of 2-bromo-1-(2,4-dichlorophenyl)-4,4-dimethyl-1-phenylsulfonylpentan-3-one and 2.23 g of triethylamine in 100 ml of acetone was refluxed for 3 hours. The mixture was poured into ice water and extracted with 150 ml of ethyl acetate. The organic layer was washed twice with water, dried over anhydrous sodium sulfate, and evaporated under reduced pressure. The residue was purified by column chromatography on silica gel using a mixture of n-hexane (20 parts) and acetone (1 part) to give 4.8 g of 1-(2,4-dichlorophenyl)-4,4-dimethyl-1-phenylsulfonyl-1-penten-3-one. n$_D^{25}$1.5723

| Elementary analysis | C (%) | H (%) | S (%) | Cl (%) |
|---|---|---|---|---|
| Found | 57.32 | 4.46 | 8.15 | 17.92 |
| Calculated (as C$_{19}$H$_{18}$O$_2$SCl$_2$) | 57.43 | 4.58 | 8.07 | 17.84 |

Method B:

Sodium ethylate was prepared by dissolving 2.3 g of metallic sodium in 100 ml of 99% ethanol, which was then mixed with 6.9 g of triazole and stirred for 30 minutes. The mixture was evaporated to dryness under reduced pressure to give sodium salt of triazole. Thus prepared sodium salt of triazole (0.91 g) was added to a solution of 2-bromo-1-(2,4-dichlorophenyl)-4,4-dimethyl-1-phenylsulfonylpentan-3-one (4.78 g) in acetonitrile (50 ml), and refluxed for 1 hour. After cooling, the mixture was added to 200 ml of ice water and extracted with ethyl acetate. The organic layer was then treated in the same manner as that of the method A to give 3.77 g of 1-(2,4-dichlorophenyl)-4,4-dimethyl-1-phenylsulfonyl-1-penten-3-one.

Method C:

To a solution of 4.44 g of 2-bromo-1-(2,4-dichlorophenyl)-4,4-dimethyl-1-phenylsulfonylpentan-3-one in 50 ml of tetrahydrofuran, a solution of 0.56 g of potassium hydroxide in 30 ml of water was added dropwise and vigorously stirred for 3 hours. The reaction mixture was combined with 100 ml of ice water, and extracted with 100 ml of chloroform. The organic solvent layer was washed twice with water, dried over anhydrous sodium sulfate, and evaporated under reduced pressure to give 3.61 g of 1-(2,4-dichlorophenyl)-4,4-dimethyl-1-phenylsulfonyl-1-penten-3-one.

EXAMPLE 13

Synthesis of 1-(2,4-dichlorophenyl)-4,4-dimethyl-1,2-bis(1,2,4-triazol-1-yl)pentan-3-one A mixture of 3.97 g of 1-(2,4-dichlorophenyl)-4,4-dimethyl-1-phenylsulfonyl-1-penten-3-one, 2.07 g of triazole, 0.69 g of potassium carbonate and 50 ml of acetonitrile was refluxed for 12 hours. After cooling, the mixture was treated in the same manner as that of Example 4 to give 4.2 g of oily substance. This substance was purified by column chromatography on silica gel to give 3.85 g of the captioned compound. $n_D^{28}$ 1.5445.

| Elementary analysis | C (%) | H (%) | N (%) | Cl (%) |
|---|---|---|---|---|
| Found | 51.85 | 4.63 | 21.43 | 17.92 |
| Calculated (as $C_{17}H_{18}N_6OCl_2$) | 51.91 | 4.62 | 21.37 | 18.03 |

EXAMPLE 14

Synthesis of 1-(2,4-dichlorophenyl)-4,4-dimethyl-1,2-bis(1,2,4-triazol-1-yl)pentan-3-one A mixture of 1.4 g of triazole, 2.8 g of potassium carbonate and 60 ml of acetonitrile was heated under reflux for 2 hours. After cooling, 4.8 g of 2-bromo-1-(2,4-dichlorophenyl)-4,4-dimethyl-1-phenylsulfonyl-pentan-3-one was added to the mixture, which was then reacted at 20° C. for 1 hour, and under reflux for 2 hours. The reaction mixture was treated in the same way as that of Example 4 to give 3.5 g of oily substance, which was purified by column chromatography on silica gel to give 3.12 g of 1-(2,4-dichlorophenyl)-4,4-dimethyl-1,2-bis(1,2,4-triazol-1-yl)pentan-3-one as oil. $n_D^{27}$ 1.5440

| Elementary analysis | C (%) | H (%) | N (%) | Cl (%) |
|---|---|---|---|---|
| Found | 51.87 | 4.71 | 21.36 | 17.89 |
| Calculated (as $C_{17}H_{18}N_6OCl_2$) | 51.91 | 4.62 | 21.37 | 18.03 |

Thus obtained product contains two diastereomer, and may further be isolated by column chromatography on silica gel. This product can be used for the next step, the heat-decomposition without any further isolation.

EXAMPLE 15

Synthesis of 1-(2,4-dichlorophenyl)-4,4-dimethyl-2-(1,2,4-triazol-1-yl)-1-penten-3-one 1-(2,4-Dichlorophenyl)-4,4-dimethyl-1,2-bis(1,2,4-triazol-1-yl)pentan-3-one (1.0 g) was heated under the same conditions as those of Example 7 and the 0.73 g of pale yellow oily substance was obtained by treating the reaction mixture in the same way as that of Example 7. Triazole 0.172 g was recovered from the aqueous layer. This oily substance was analyzed by gas chromatography under the same conditions as Example 7, and two peaks (peack area 37/63) due to the E- and Z-isomers were observed.

| Elementary analysis data of the substance: | C (%) | H (%) | N (%) | Cl (%) |
|---|---|---|---|---|
| Found | 55.41 | 4.55 | 13.10 | 21.72 |
| Calculated (as $C_{15}H_{14}N_3OCl_2$) | 55.56 | 4.67 | 12.96 | 21.87 |

The NMR spectrum of the substance is the combination of the signals of the E- and Z-isomers.

The E- and Z-isomers of 1-(2,4-dichlorophenyl)-4,4-dimethyl-2-(1,2,4-triazol-1-yl)-1-penten-3-one have the following NMR spectrums.

| Isomer | NMR Spectrum |
|---|---|
| E-Isomer m.p. 92–93° C. | 8.30 (1H,s,triazole-proton) |
| | 8.04 (1H,s,triazole-proton) |
| | 7.26 (2H,m,phenyl-proton) |
| | 7.45 (1H,m,phenyl 3-position proton) |
| | 7.22 (1H,s,olefin-proton) |
| | 0.97 (9H,s,butyl-proton) |
| Z-Isomer m.p. 119–120° C. | 7.94 (1H,s,triazole-proton) |
| | 7.80 (1H,s,triazole-proton) |
| | 7.46 (1H,s,olefin-proton) |
| | 7.33 (1H,d,phenyl 3-position proton, J = 3 Hz) |
| | 6.95 (1H,d,phenyl 5-position proton, J = 3 Hz, 8 Hz) |
| | 6.40 (1H,d,phenyl 6-position proton, J = 8 Hz) |
| | 1.27 (9H,s,butyl-proton) |

EXAMPLE 16

Synthesis of 1-(2,4-dichlorophenyl)-1-p-toluene-sulfonyl-4,4-dimethylpentan-3-one Step 1: Synthesis of 1-(2,4-dichlorophenyl)-1-p-methylphenylthio-4,4-dimethylpentan-3-one:

A mixture of 50 g of 2,4-dichlorobenzalpinacolone, 25 g of p-methylphenylthiol, 0.5 g of Triton-B and 400 ml of ethanol was heated under reflux for 4 hours. After the removal of the solvent by distillation under reduced pressure, 300 ml of ice water was added to the residue and extracted with ether. The ether layer was washed with 5% potassium carbonate aqueous solution and evaporated. The residue was added to 100 ml of n-hexane to give 70 g of crystalline 1-(2,4-dichlorophenyl)-1-p-methylphenylthio-4,4-dimethylpentan-3-one. m.p. 65°–66° C.

Step 2: Synthesis of 1-(2,4-dichlorophenyl)-1-p-toluenesulfonyl-4,4-dimethylpentan-3-one:

To a solution of 20 g of 1-(2,4-dichlorophenyl)-1-p-methylphenylthio-4,4-dimethylpentan-3-one in 500 ml of dichloromethane, 20 g of m-chloroperoxybenzoic acid was added at −5° C., and the mixture was stirred at a room temperature for 3 hours. The reaction mixture was washed with 5% sodium hydrogensulfite aqueous solution and with sodium bicarbonate aqueous solution, and evaporated to give 21 g of the captioned compound. $n_D^{27}$ 1.5563.

EXAMPLE 17

In the same nanner as in Example 16, but using p-chlorophenylthiol instead of p-methylphenylthiol, 1-

(2,4-dichlorophenyl)-1-(4-chlorophenylthio)-4,4-dimethylpentan-3-one, m.p. 122°–123° C. and 1-(2,4-dichlorophenyl)-1-(4-chlorophenylsulfonyl)-4,4-dimethylpentan-3-one, m.p. 184°–185° C. were obtained.

EXAMPLE 18

Synthesis of 1-(4-chlorophenyl)-4,4-dimethyl-1-p-toluenesulfonyl-pentan-3-one

A mixture of 3 g of 4-chlorobenzalpinacolone, 2 g of p-toluenesulfinic acid and 15 ml of ethanol was refluxed for 8 hours and then allowed to stand at a room temperature overnight. The collection of the precipitated crystals gave 4.8 g of the captioned compound (yield: 94%). m.p. 170°–171° C.

EXAMPLE 19

Synthesis of 1-(2,4-dichlorophenyl)-4,4-dimethyl-1-p-toluenesulfonylpentan-3-one A mixture of 10 g of 2,4-dichlorobenzalpinacolone, 7.3 g of p-toluenesulfinic acid, 4.1 g of $NaH_2PO_3$ and 70 ml of 90% aqueous alcohol was heated under reflux for 8 hours. After cooling, 400 ml of ice water was added to the reaction mixture and extracted with 500 ml of ethyl acetate. The organic solvent layer was washed with 400 ml of 5% sodium bicarbonate aqueous solution and 400 ml of ice water and evaporated under reduced pressure to give 16 g of the captioned compound (yield 99%). $n_D^{27}$ 1.5563.

EXAMPLE 20

The bromination of 1-(2,4-dichlorophenyl)-1-p-toluenesulfonyl-4,4-dimethylpentan-3-one was carried out in the same manner as that of Example 3 but using 25 g of 1-(2,4-dichlorophenyl)-1-p-toluenesulfonyl-4,4-dimethyl-3-one, 9.2 g of bromine, 200 ml of acetic acid and 300 ml of chloroform, and 29 g of 2-bromo-1-(2,4-dichlorophenyl)-4,4-dimethyl-1-p-toluenesulfonylpentan-3-one was obtained.

EXAMPLE 21

The bromination of 1-(2,4-dichlorophenyl)-4,4-dimethyl-1-(4-chlorophenylsulfonyl)-pentan-3-one was carried out in the same manner as that of Example 3 but using 25 g of 1-(2,4-dichlorophenyl)-1-(4-chlorophenylsulfonyl)-4,4-dimethylpentan-3-one, 8.9 g of bromine, 200 ml of acetic acid and 300 ml of chloroform, and 24.4 g of 2-bromo-1-(2,4-dichlorophenyl)-4,4-dimethyl-1-(4-chlorophenylsulfonyl)pentan-3-one was obtained. m.p. 184°–185° C.

EXAMPLE 22

Synthesis of 1-(2,4-dichlorophenyl)-4,4-dimethyl-1-p-toluenesulfonyl-1-penten-3-one Method A:

To a solution of 1 g of 2-bromo-1-(2,4-dichlorophenyl)-4,4-dimethyl-1-p-toluenesulfonylpentan-3-one in 30 ml of tetrahydrofuran, a solution of 0.12 g of potassium hydroxide in 10 ml of water was added dropwise under ice-cooling. The mixture was stirred under ice-cooling for 3 hours. After adding 100 ml of water, the mixture was extracted with 100 ml of chloroform. The chloroform layer was evaporated under reduced pressure, and the residue was crystallized with n-hexane to give 0.5 g of the captioned compound. m.p. 104°–105° C.

Method B:

To a solution of 4.9 g of 2-bromo-1-(2,4-dichlorophenyl)-4,4-dimethyl-1-p-toluenesulfonylpentan-3-one in a mixture of 150 ml of acetonitrile and 150 ml of tetrahydrofuran, 1.0 g of sodium salt of triazole was added. The mixture was stirred under ice-cooling for 5 hours. After the addition of 500 ml of water, the mixture was extracted with 500 ml of chloroform. The chloroform layer was evaporated, and the residue was crystallized with n-hexane to give 4 g of the captioned compound. m.p. 104°–105° C.

EXAMPLE 23

Synthesis of 1-(2,4-dichlorophenyl)-4,4-dimethyl-1,2-bis(1,2,4-triazol-1-yl)pentan-3-one Method A:

With the same procedures as those of Example 4 but using 5 g of 2-bromo-1-(2,4-dichlorophenyl)-4,4-dimethyl-1-p-toluenesulfonylpentan-3-one, 1.4 g of triazole, 2.8 g of potassium carbonate, and 60 ml of acetone, 3.2 g of the captioned compound was obtained as oily substance. $n_D^{27}$ 1.5440.

Method B:

With the same procedures as those of Example 4 but using 5 g of 2-bromo-1-(2,4-dichlorophenyl)-4,4-dimethyl-1-(4-chlorophenylsulfonyl)pentan-3-one, 1.4 g of triazole, 2.8 g of potassium bicarbonate and 60 ml of acetonitrile, 2.9 g of the captioned compound as oily substance was obtained.

Method C:

With the same procedures as those of Example 13 but using 2 g of 1-(2,4-dichlorophenyl)-4,4-dimethyl-1-p-toluenesulfonyl-1-penten-3-one, 1 g of triazole, 0.35 g of potassium carbonate and 50 ml of acetonitrile, 1.8 g of the captioned compound was obtained.

The present compounds (II)–(VI) obtained by above methods are shown in Table 1.

TABLE 1

| Compound of the formula | X | Y | Physical constant |
|---|---|---|---|
| (II) | H | — | mp 157–161° C. |
|  | Cl | — | $n_D^{28}$ 1.5445 |
| (III) | H | H | mp 135–136° C. |
|  | H | CH$_3$ | mp 91–92° C. |
|  | Cl | Cl | mp 97–98° C. |
|  | Cl | H | $n_D^{25}$ 1.5723 |
|  | Cl | CH$_3$ | mp 104–105° C. |
| (IV) | H | H | mp 167–168° C. |
|  | H | CH$_3$ | mp 167–168° C. |
|  | Cl | Cl | mp 184–185° C. |
|  | Cl | H | mp 135–136° C. |
|  | Cl | CH$_3$ | mp 175–176° C. |
| (V) | H | H | mp 145–146° C. |
|  | H | CH$_3$ | mp 170–171° C. |
|  | Cl | Cl | mp 184–185° C. |
|  | Cl | H | mp 112–113° C. |
|  | Cl | CH$_3$ | $n_D^{27}$ 1.5563 |
| (VI) | H | H | mp 127–128° C. |
|  | H | CH$_3$ | mp 65–66° C. |
|  | Cl | Cl | mp 122–123° C. |
|  | Cl | H | mp 79–80° C. |

What is claimed is:

1. A process for producing a compound of the formula:

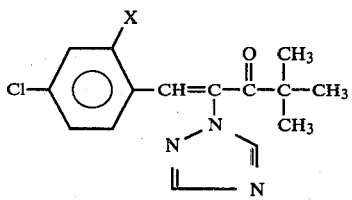

(I)

wherein X is a hydrogen or chlorine atom, which comprises heating a compound of the formula:

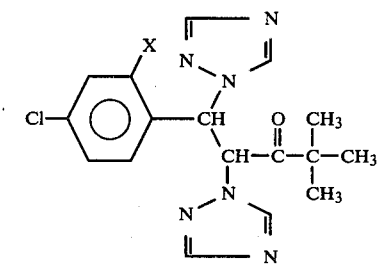

(II)

wherein X is as defined above.

2. The process according to claim 1, wherein the heating is carried out at 50° to 200° C.

3. The process according to claim 2, wherein the heating is carried out in the presence of a solvent of ketones, halogenated hydrocarbons, aromatic hydrocarbons, nitriles, ethers, dimethylformamide, dimethylsulfoxide, hexamethylphosphoramide or water.

4. The process according to claim 1, which further comprises a step of reacting a compound of the formula:

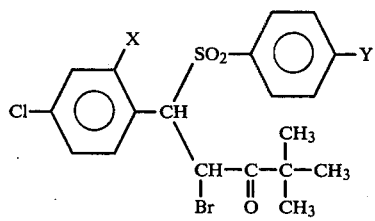

(IV)

wherein X is as defined in claim 1, and Y is a hydrogen or chlorine atom or a methyl group, with triazole to give the compound of the formula (II).

5. The process according to claim 1, which further comprises a step of reacting a compound of the formula:

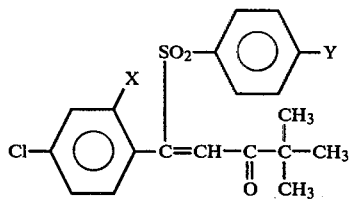

(III)

wherein X is as defined in claim 1, and Y is a hydrogen or chlorine atom or a methyl group, with triazole to give the compound of the formula (II).

6. The process according to claim 5, which further comprises a step of reacting a compound of the formula:

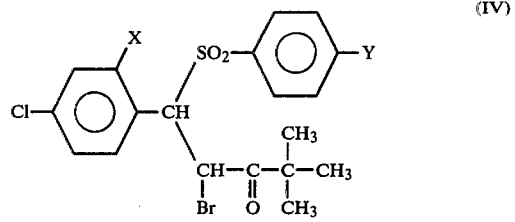

(IV)

wherein X and Y are as defined in claim 5, with a base to give the compound of the formula (III).

7. The process according to claim 4, 5 or 6, wherein the reaction is carried out in the presence of a base selected from the group consisting of carbonates, acetates, hydroxides of metals and tertiary amines, in a solvent selected from the group consisting of ketones, nitriles, aromatic hydrocarbons, ethers, dimethylformamide, dimethylsulfoxide, hexamethylphosphoramide and water, at 0° C. to the boiling point of the solvent employed.

8. The process according to claim 4, which further comprises a step of reacting a compound of the formula:

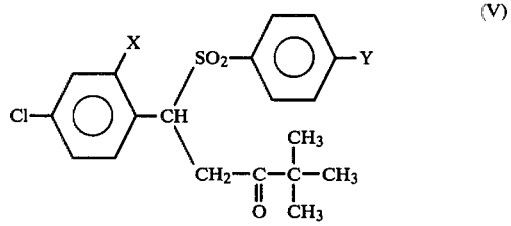

(V)

wherein X and Y are as defined in claim 4, with a brominating agent to give the compound of the formula (IV).

9. The process according to claim 8, wherein the brominating agent is bromine or N-bromosuccinimide.

10. The process according to claim 8, wherein the reaction is carried out in a solvent selected from the group consisting of halogenated hydrocarbons, halogenated aromatic hydrocarbons, ethers, water, methanol, pyridine, dimethylformamide and acetic acid, at 0° C. to the boiling point of the solvent employed.

11. The process according to claim 6, which further comprises a step of reacting a compound of the formula:

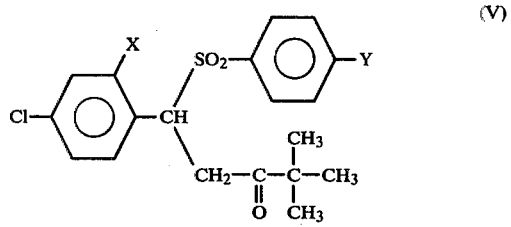

(V)

wherein X and Y are as defined in claim 6, with a brominating agent to give the compound of the formula (IV).

12. The process according to claim 11, wherein the brominating agent is bromine or N-bromosuccinimide.

13. The process according to claim 11, wherein the reaction is carried out in a solvent selected from the group consisting of halogenated hydrocarbons, halogenated aromatic hydrocarbons, ethers, water, methanol, pyridine, dimethylformamide and acetic acid, at 0° C. to the boiling point of the solvent employed.

14. The process according to claim 6, which further comprises a step of reacting a compound of the formula:

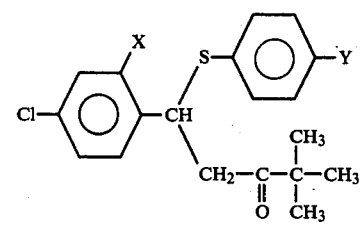
(VI)

wherein X and Y are as defined in claim 8, with an oxidizing agent to give the compound of the formula (V).

15. The process according to claim 11, which further comprises reacting a compound of the formula:

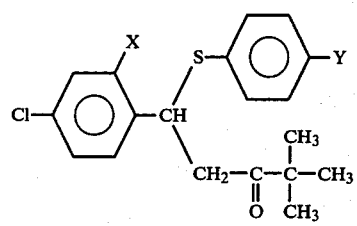
(VI)

wherein X and Y are as defined in claim 11, with an oxidizing agent to give the compound of the formula (V).

16. The process according to claim 14 or 15, wherein the oxidizing agent is hydrogen peroxide, organic acid peroxides, potassium permanganate, sodium metaperiodate, nitric acid, sodium hypochlorite, ozone or chromic acid.

17. The process according to claim 14 or 15, wherein the reaction is carried out in a solvent selected from the group consisting of halogenated hydrocarbons, ketones, acetic acid and water, at −50° to 100° C.

18. The process according to claim 8, which further comprises a step of reacting a compound of the formula:

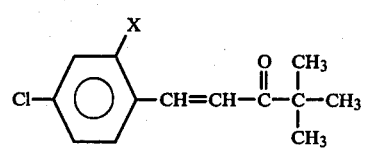
(VII)

wherein X is as defined in claim 8, with a compound of the formula:

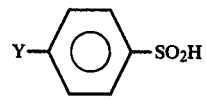

wherein Y is as defined in claim 8, to give the compound of the formula (V).

19. The process according to claim 11, which further comprises a step of reacting a compound of the formula:

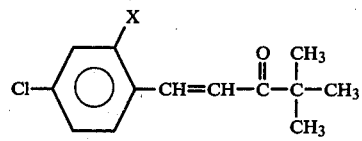
(VII)

wherein X is as defined in claim 11, with a compound of the formula:

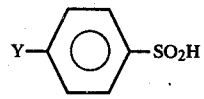

wherein Y is as defined in claim 11, to give the compound of the formula (V).

20. The process according to claim 18 or 19, wherein the reaction is carried out in a solvent selected from the group consisting of alcohols, hydrocarbons, ketones, nitriles, ethers, dimethylformamide, dimethylsulfoxide, water and mixtures thereof, at 0° C. to the boiling point of the solvent employed.

21. The process according to claim 18 or 19, wherein the reaction is carried out in the presence of a base of pyridine, Triton B or sodium phosphite.

* * * * *